United States Patent [19]

Dobbins

[11] Patent Number: 5,013,752

[45] Date of Patent: * May 7, 1991

[54] PREVENTION AND TREATMENT OF ALCOHOLISM BY THE USE OF DIETARY CHROMIUM

[76] Inventor: John P. Dobbins, 615 Allen Ave., San Marino, Calif. 91108

[*] Notice: The portion of the term of this patent subsequent to Apr. 17, 2007 has been disclaimed.

[21] Appl. No.: 509,214

[22] Filed: Apr. 16, 1990

Related U.S. Application Data

[63] Continuation-in-part of Ser. No. 321,780, Mar. 10, 1989, Pat. No. 4,918,102.

[51] Int. Cl.⁵ .................... A61K 33/24; A23G 3/00
[52] U.S. Cl. .................... 514/505; 514/810; 514/811; 424/155; 426/306
[58] Field of Search .................. 514/505, 810, 811; 424/655; 426/306

[56] References Cited

U.S. PATENT DOCUMENTS

| | | | |
|---|---|---|---|
| 4,006,219 | 2/1977 | Upham et al. | 424/94.1 |
| 4,315,927 | 2/1982 | Evans | 514/188 |
| 4,543,262 | 9/1985 | Michnowski | 426/306 |
| 4,918,102 | 4/1990 | Dobbins | 514/505 |

FOREIGN PATENT DOCUMENTS 8701285 3/1987 PCT Int'l Appl. .

Primary Examiner—Shep K. Rose
Assistant Examiner—Kevin Weddington
Attorney, Agent, or Firm—William W. Haefliger

[57] ABSTRACT

Prevention of or therapeutically curing the disease of alcoholism comprises supplementing the diet with biologically available chromium, such as naturally occurring chelated chromium. A food bar containing chromium picolinate is also disclosed.

7 Claims, No Drawings

PREVENTION AND TREATMENT OF ALCOHOLISM BY THE USE OF DIETARY CHROMIUM

This application is a continuation-in-part of Ser. No. 321,780 filed Mar. 10, 1989, now U.S. Pat. No. 4,918,102.

BACKGROUND OF THE INVENTION

1. Field of the Invention

This invention relates generally to the treatment of alcoholism, and more particularly, to supplementing the diet with assimilable chelated chromium, for this purpose.

The assimilation of an adequate quantity of physiologically important micronutrients is essential to the health of both humans and animals. Failure of the body to ingest and absorb the necessary amounts of essential micronutrients (e.g., vitamins and/or minerals) can lead to improper functioning of the metabolic processes as well as to a variety of diseases and associated symptoms. For example, anemia is correlated with an iron deficiency, and goiter is correlated with an iodine deficiency.

2. Description of Prior Art

Dr. Walter Merz of the Human Nutrition Laboratory in Bethesda, Md., was the first scientist to describe the occurrence and function of chromium in biological systems (Physiological Rev. 49:163, 1969). This was followed in 1970 by the proclamation of Dr. Henry A. Schroeder, Professor of Physiology Emeritus at the Darmouth Medical School, that chromium deficiency was a factor in atherosclerosis (Jour. Chronic Diseases 23:123). Regrettably, this knowledge was not then recognized, accepted, and applied to medical practice. Most recently, Gary W. Evans, PhD, and Muriel B. Gilman at Bemidji State University, Mont. 56601, have prepared a paper (for 1989 publication in one of the journals of the American Chemical Society) titled "Anabolic Effect of Chromium Picolinate". Therein they identify metabolic mechanisms showing how ingestion of naturally occurring chromium beneficially decreases LD ("bad") cholesterol and increases HD ("good") cholesterol in blood serum. They link these observations to "death from heart disease" and to treatment and prevention of diabetes.

3. Chromium Deficiency

Average Americans are at far greater risk for being afflicted with hypoglycemia and/or diabetes than most foreigners. This is because many have overindulged in sugar consumption (over 5 ounces/day) throughout their life times. They have thereby excessively reduced their reserve supplies of chromium in their bodies—amounts with which they were amply provided at birth. Comparison of chromium concentrations in the tissues of Americans and foreigners of all ages showed chromium to be present in all young bodies. It was not detected in 15-23 percent of tissues from Americans over 50 years old but was found in the bodies of almost every foreigner (98.5%). Estimates based on organ weights indicated that native Africans had twice, Near Easterners 4.4 times, and Orientals five times as much chromium in their bodies as did Americans (ref. Schroeder, p. 73). Blood chromium has not been shown to reflect tissue stores. Very few foods contain readily assimilable chromium compounds capable of replenishing bodies drained and depleted of essential GTF. The trace metal chromium-in its trivalent ($Cr+++$) chelated form, known as GTF (Glucose Tolerance Factor)—is indispensable for burning blood-sugar Since adequate synthesis of GTF in the human body is questionable, Dr. Pfeiffer declared that this compound be assigned full-fledged vitamin status. Pure GTF is completely non-toxic. Mothers—to protect their babies and give them a good start in life—sacrificially transfer much of the residual chromium in their bodies to their growing fetuses. Placental tissue has the highest measured level of chromium in the body. American women after several pregnancies usually exhibit greatly reduced Cr-levels in their bodies.

4. Alcoholism and Hypoglycemia

Other than the recognition by physicians and scientists that hypoglycemia (a glucose intolerance disease) consistently accompanies the disease of alcoholism, there was no prior identification in the medical literature of alcoholism as a consequence of chromium deficiency. In fact, a recent pertinent declaration by Dr. William Mayer, Assistant Secretary of Defense for Health and Welfare, and head of the premier American alcoholic research agency—the Alcoholic, Drug Abuse, and Mental Health Administration, Washington, D.C.—states (ref. Babor, p. 197):

"Then there are 'magic bullets' such as insulin for diabetes, a drug that controls an otherwise devastating metabolic disease. We don't see signs of any such 'miracle drug' in the field of treatment for alcoholics."

This invention denies the continuing validity of that statement.

5. Genetic and Psychological Factors

The existence of genetic predisposition to alcoholism is long established. It has a factual physiological basis. Mental illness as a factor is not eliminated; but, for most alcoholics, it can now be relegated to a minor role. The new knowledge disclosed by this invention allows us to affirm unequivocally: Craving for alcohol is NOT due to moral weakness. It is a sickness—the conditioned response of the body to a pathological lack in the diet of the essential trace element chromium.

SUMMARY OF THE INVENTION

I have discovered that the physiological disorder of alcoholism is due to the body's deficiency of the essential metal chromium. This pathological condition of chromic deficiency is herein called hypochromism. Based upon my discovery of the cause-and-effect relationship between hypochromism and alcoholism, I claim that the disease of alcoholism can be prevented and/or therapeutically cured by replenishing the body's depleted supply of the trace element chromium. This particular micronutrient is the most deficient of all micronutrients (vitamins and minerals) in the diet of Americans. The major cause of hypochromism is excessive consumption of sucrose (ordinary table sugar).

DETAILED DESCRIPTION

Applicant's familiarity with chromium deficiency (which results mostly from ingestion of sugar and/or glucose) and with its direct connection to cardiovascular disease as the major cause of death in this country stimulated further studies and medical observations. Results of these observations supplied the background information necessary for the conclusions presented in this disclosure.

Pertinent details of such background knowledge are next cited:

(a) Functional hypoglycemia (not due to dysfunction of glands) and adult-onset diabetes mellitis (hyperglycemia dysinsulinism) are the two most familiar manifestations of blood-sugar disorders (glucose intolerance). The delicate balance between these two abnormal states of health is maintained by GTF working with the hormones insulin (Pfeiffer, pp. 290-1) and glucagon.

(b) These disorders are caused by hypochromism (depleted supplies of chromium in the body). Alcoholism is here claimed and shown below to have the same cause. Beasley (p. 77) states: "Undoubtedly the commonest cause of hypoglycemia . . . is overindulgence in alcohol."

(c) Women are more subject to these intolerances than are men. These symptoms are regularly observed in parous women (those who have given birth to children). Pregnant women also commonly exhibit gestational diabetes (blood-sugar levels in excess of 120 mg %). For example, two young women in their eighth month of pregnancy exhibited blood-sugar levels of 140 mg % and 180 mg %. The first, after taking prescribed chromium supplements of 100 μg tablets (GTF complex from yeast), one with each meal for 10 days (a total of $30 \times 100$ μg = 3000 μg = 3 mg) dropped her glucose blood level down to 80 mg %, and the second expectant mother on the same prescription dropped her level down to 90 mg % in two weeks' time. The natural (d) Carl C. Pfeiffer, PhD, MD, Director of condition for normal persons is to maintain a fasting level of 70 to 100 mg % of glucose in the blood. Princeton's Brain Bio Center, states (ref, p. 290): "Many women in Western countries are so deficient in chromium that the white blood cell chromium level may decrease by 50 percent with each pregnancy, resulting first in complete alcohol intolerance and later in glucose intolerance (adult-type diabetes).

(e) A pertinent statistic on alcoholism quoted by Beasley (ref, p. 30) is: "twice as many black women as black men report health problems due to drinking". This result follows qualitatively as a logical consequence from items (b), (c), and (d) above. The higher quantitive proportions (women/men=2:1) reflect primarily higher birth rates among the black population than among other racial groups, rather than necessarily indicate a higher rate of alcohol consumption among black than non-black cohorts.

BIOLOGICALLY AVAILABLE CHROMIUM

Ordinary foods consumed in the diet of average Americans contain such low levels and low quality of assimilable chromium that losses greatly exceed the intake of this needed metal for the reasons explained earlier (see paraqraph #3). The best-known natural source of nutritional chromium is brewer's yeast grown on blackstrap molasses. A better food supplement holding much higher levels of chelated chromium has been GTF Complex sold in healthfood stores. Most of the population of the Westernized world—the inhabitants of the industralized nations—are afflicted with chronic (slow-acting) hypochromism, reflected by cardiovascular and related diseases.

Alcoholism can be regarded as the manifestation of severely acute hypochromism. In this regard, there has been failure to recognize that sucrose acts as a chronic toxin by cumulatively extracting essential chromium from the body, thereby shortening life. The toxic effects of ingesting sucrose have been previously reported by J. P. Dobbins (J. Nat. Health Federation, Vol. 7, Nos. 3 and 4, 1988, and in the September 1987 publication *Hypoclycemia. Violent Crime, and the Dangers of Sugar*, Philosanus, 326 East Colorado Boulevard, Suite 103, Pasadena, Calif. 91101).

In accordance with the present invention, it has been found that chromium intake into the body can be accelerated and greatly increased by consumption of chromium picolinate, known commercially as CHROMAX II, as cited in U.S. Pat. Ser. No. 4,315,927, and sold by Nutrition 21. It is found naturally in the body and is characterized by a high rate of assimilation into the blood serum.

TREATMENT FOR ALCOHOLICS

The recommended simple procedure is to consume food supplement tablets of readily assimilable chelated chromium (earlier "GTF Complex", but now preferably high-potency GTF, the latest CHROMAX II) for a sufficient length of time to replenish the body's depleted reserve supply. This involves continuing the ingestion of GTF until the level of chromium in body tissues reaches or exceeds that present at birth—its highest point. For most Americans, this is a minimum of 2½ parts per billion (ppb)—equivalent to a total of 1.4 mg in the body of a normal 70 kg Western adult or to a level of 12 ppb—equivalent to a total of 7 mg in the body of a mainland Chinese. The diagnostic procedure for determining this level is preferably by means of spectrographic hair analysis (see Passwater, pp. 24-25). Blood analysis is a less reliable, less meaningful, and less easily performed test than hair analysis. For an alcoholic, the cessation of his craving for ethanol is a good indicator that he has achieved minimum replacement of his needed stores. (He has in effect refilled his "overdrawn bank account", so that he is again capable of meeting normal daily demands of stress or anxiety without having to resort to the harmful temporary crutch of sugar or alcohol, or to the equivalent adrenaline-stimulating drugs, caffeine, theophylline, nicotine—in coffee, tea, or tobacco. These alkaloid drugs briefly elevate the blood-sugar levels, but their long-term effects are to act as depressants for the nervous system.)

Further, the presence of adequate reserve supplies of GTF in the body aids the opposite-acting pancreatic hormones insulin and glucagon to stabilize more rapidly the body's glucose blood level within its normal range of 70-100 mg/100 ml.

Accordingly, the method of preventing and/or therapeutically curing the disease of alcoholism comprises the step of supplementing the diet with biologically available chromium. Such chromium is most preferably chelated chromium, which may be synthetically-produced chromium picolinate. This is an orthomolecular (nondrug) medicine having the formula

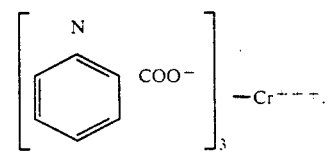

Such supplementing of the diet is continued until the blood glucose level is brought to normal or substantially normal level, as at birth. Such supplementing is typically carried out by ingesting a daily average amount of between about 150 and 250 micrograms of chelated chromium over a period of days until the blood glucose level is brought to normal or substantially normal level. The ingested chromium picolinate is preferably in compressed powder tablet or free powder capsule form.

There usually exists a large time-lag of about 10 to 20 years before new knowledge discovered by medical scientists about health and disease reaches the medical schools, is taught to aspiring physicians, and finally is applied in practice to benefit the general public. To illustrate this point, the so-called "bible of medicine", used as a standard reference book by physicians, and college text by medical students, is: Harrison's *Principles of Internal Medicine*, McGraw Hill. Its latest version (11th edition, 1988) in the section devoted to "Diabetes Mellitus and Hypoglycemia" makes no mention yet of chromium in relation thereto, nor is the common condition of gestational diabetes recognized. This same absence of important information about medical benefits of treating patients with nutrient chromium characterizes the competitive *Textbook of Internal Medicine*, edited by W. N. Kelley, M.D., and published by Lippincott Co. (1st edition 1989). J. D. Beasley on p. 12 of his 1987 book *Wrong Diagnosis, Wrong Treatment: The Plight of the Alcoholic in America* (publ. by Essential Medical Information Systems, Inc., N.Y.) identifies "alcoholism as a . . . genetic/metabolic disorder more closely related to diabetes than to any behavioral disorder" (emphasis added). Nowhere in his book is chromium mentioned. Had Walter Merz or Henry Schroeder about 15 years ago applied for and received a patent on the application of their knowledge to treat and/or cure sugar-related diseases, then this kind of therapy would possibly have become widespread by now, and much suffering could have been alleviated.

A final word applied to the subject of chromium deficiency is from Dr. Schroeder (page 84) who says: "Modern man makes many mistakes through lack of knowledge, but there is no excuse for his continuing his mistakes in the face of knowledge."

The herein method of preventing and/or therapeutically treating the disease of alcoholism, by supplementing the diet with synthetically produced nutrient chromium picolinate at levels of over 50 μg, (the minimum US RDA) also contemplates the provision of such chromium picolinate in a food bar now lacking any added chromium. Typical of such food bars are those 200-calorie bars used for weight control "providing 100% US RDA of 10 essential vitamins and 2 essential minerals plus significant amounts of 3 additional minerals and protein", as manufactured and sold by Nutrilite, division of Amway.

|  | Quantity | % U.S. RDA |
|---|---|---|
| Protein | 10 g | 15 |
| VITAMINS | | |
| Vitamin A | 5,000 I.U. | 100 |
| Vitamin D | 400 I.U. | 100 |
| Vitamin E | 30 I.U. | 100 |
| Vitamin C | 60 mg | 100 |
| Folic Acid | 4 mg | 100 |
| Thiamine (B-1) | 1.5 mg | 100 |
| Riboflavin (B-2) | 1.7 mg | 100 |
| Niacin | 20 mg | 100 |
| Vitamin B-6 | 2 mg | 100 |
| Vitamin B-12 | 6 mcg | 100 |

|  | Quantity | % U.S. RDA |
|---|---|---|
| MINERALS | | |
| Calcium | 3 g | 30 |
| Phosphorus | 3 g | 30 |
| Iodine | 150 mcg | 100 |
| Iron | 18 mg | 100 |
| Magnesium | 120 mg | 30 |
| Chromium Picolinate | 100 μg | 100 |

Ingredients: High Fructose Corn Syrup, Dehydrated Apples, Whey Protein, Textured Soy Flour, Fructose, Partially Hydrogenated Vegetable Oil (from Cotton, Soy, Palm, Palm Kernel), Soy Protein Isolate, Corn Bran, Natural Flavors, Vital Wheat Gluten-Dicalcium Phosphate, Non Fat Milk Solids, Cinnamon, Magnesium Oxide, Whey Solids, Lecithin, Ascorbic Acid, Ferrous Fumarate, Vitamin E Acetate, Sodium Caseinate, Niacinamide, Vitamin A, Palmitate, Vitamin B-12, Pyridoxine Hydrochloride, Riboflavin, Ethycellulose, Thiamine Mononitrate, Calcium Sulfate, Folic Acid, Potassium Iodine, Ergocalciferol.

A 100% water soluble form of chromium picolinate may be used in the food bar of the EXAMPLE. That soluble form is chromium picolinate complexed with hydroxypropyl Beta-cyclodextrine, and is produced by Nutrition 21, San Diego, Calif. It may be substituted in like amount for the chromium picolinate recited in the EXAMPLE. Each food bar as defined in the EXAMPLE preferably contains between about 100 and 250 μg of chromium picolinate, or that amount of chromium picolinate complexed with hydroxypropyl Betacyclodextrine.

The method of the invention also anticipates treating acute hypochromism parenterally, not through the alimentary canal (but rather by injection through some other route, as subcutaneous, intramuscular, intravenous, etc.) with an aqueous solution of chromic picolinate.

I claim:

1. An edible food bar containing protein, carbohydrate, fat, vitamins, and minerals, said minerals including at least about 50 micrograms of chromium picolinate.

2. At least one edible food bar as defined in claim 1 adapted for the method of treating the disease of alcoholism by supplementing the diet with naturally occurring but synthetically produced nutrient chromium picolinate in the form of tablets or capsules, said supplementing being carried out by administering a daily average amount of between about 150 and 250 micrograms of chromium picolinate over a period of days until the blood glucose level is brought to normal or substantially normal level.

3. The edible food bar of claim 1 wherein the bar contains between about 100 and 250 micrograms of chromium picolinate.

4. At least 20 food bars as defined in claim 1, to be ingested one bar per day for at least 20 days.

5. At least 20 food bars as defined in claim 2, to be ingested one bar per day for at least 20 days.

6. An edible food bar containing protein, carbohydrate, fat, vitamins, and minerals, said minerals including at least about 50 micrograms of chromium picolinate, the chromium picolinate being complexed with hydroxypropyl beta-cyclodextrine.

7. The food bar of claim 1 wherein the bar contains between about 100 to 250 micrograms of chromium picolinate.

* * * * *